United States Patent [19]

Deuel

[11] Patent Number: 5,001,064
[45] Date of Patent: Mar. 19, 1991

[54] PHOSPHATIDYLINOSITOL 4-KINASE

[75] Inventor: Thomas F. Deuel, St. Louis, Mo.

[73] Assignee: Washington University, St. Louis, Mo.

[21] Appl. No.: 208,429

[22] Filed: Jun. 20, 1988

[51] Int. Cl.$^5$ .............................................. C12N 9/12
[52] U.S. Cl. ................................................. 435/194
[58] Field of Search ............................ 435/194, 240.2

[56] References Cited

PUBLICATIONS

Thompson et al., Partial Purification and Characterization of Phosphatidylorositol Kinase from Bovine Brain, Neurochemical Research, 13(5), 1988, pp. 417–421.
Berridge and Irvine, Nature 312, 315–319 (1984).
Nishizuka, Science 225, 1365–1369 (1984).
Majerus et al., Science 234, 1519–1526 (1986).
Saltiel et al., Biochem. J. 241, 759–763 (1987).
Kaplan et al., Cell 50, 1021–1029 (1987).
Courtneidge and Heber, Cell 50, 1031–1037 (1987).
Harwood and Hawthorn, Biochem. Biophys. Acta 171, 75–88 (1969).
Endemann et al., Biochemistry 26, 6845–6852 (1987).
Whitman et al., Nature 332, 644–646 (1988).

Primary Examiner—Douglas W. Robinson
Assistant Examiner—Carol Geckle
Attorney, Agent, or Firm—Scott J. Meyer; James W. Williams, Jr.

[57] ABSTRACT

A novel phosphatidylinositol 4-kinase isolated from bovine uterus having the following characteristics:
(a) molecular weight of about 55 kDa as determined by sodium dodecylsulfate polyacrylamide gel electrophoresis;
(b) $K_m$ of about 18 μM for ATP;
(c) $K_m$ of about 22 μg/ml for phosphatidylinositol;
(d) pH optimum of about 6.0 to 7.0;
(e) activated by $Mg^{2+}$;
(f) inhibited by $Ca^{2+}$;
(g) utilizes ATP and 2'-dioxy-ATP as phosphoryl donors and specifically phosphorylates phosphatidylinositol on the 4-position; and
(h) essentially free of phosphatidylinositol-4-phosphate 5-kinase activity determined by treatment with phorphoryl donors ADP, GTP, ITP or CTP.

1 Claim, 6 Drawing Sheets

PHOSPHATIDYLINOSITOL 4-KINASE

Background of the Invention

This invention relates to a novel enzyme and, more particularly, to a highly purified phosphatidylinositol 4-kinase.

In recent years considerable effort has been made in the study of receptors that generate intracellular signals from inositol lipids. It is known that external signals induced by polypeptide growth factors may be transmitted to intracellular targets via products of inositol phospholipids (phosphoinositides) which function as second messengers. Two important such second messengers known to be produced from phosphoinositides are 1,2-diacylglycerol (1,2-DG) and inositol 1,4,5-triphosphate [Ins(1,4,5)P$_3$].

The metabolic pathways of phosphoinositides to form second messengers have been reviewed in considerable detail by various investigators. See, for example, Berridge and Irvine, *Nature* 312, 315-319 (1984); Nishizuka, *Science* 225, 1365-1369 (1984); Majerus et al., *Science* 234, 1519-1526 (1986); and references cited in these publications.

The phosphoinositides are formed from phosphatidy inositol (PtdIns) by catalytic action of kinases. Thus, phosphatidylinositol 4,5-diphosphate (PtdIns-4,5-P$_2$) is formed by the sequential phosphorylation of PtdIns through action of lipid kinases, namely phosphatidylinositol 4-kinase (PtdIns 4-kinase) and phosphatidylinositol-4-phosphate 5-kinase (PtdIns-4-P 5-kinase). In this two-stage phosphorylation, PtdIns is first phosphorylated at the 4-position by PtdIns 4-kinase to form phosphatidylinositol 4-phosphate (PtdIns-4-P) which in turn is further phosphorylated at the 5-position by PtdIns-4-P 5-kinase to give PtdIns-4,5-P$_2$.

Cleavage of the PtdIns-4,5-P$_2$ by another enzyme, phospholipase C, results in the formation of the above named second messengers, namely 1,2-DG and Ins(1,4,5)P$_3$. 1,2-DG is an activator of protein kinase C. Ins(1,4,5)P$_3$ functions to mobilize calcium from intracellular stores. The intracellular levels of these second messengers are determined by a balance between their rate of formation and their rate of removal by pathways which channel then back to PtdIns.

Brief Description of the Invention

In accordance with the present invention, a novel phosphatidylinositol 4-kinase has been isolated from bovine uterus and characterized as follows:

The phosphatidylinositol 4-kinase (PtdIns 4-kinase) has an apparent molecular weight of about 55 kilodaltons (kDa) as determined by sodium dodecylsulfate polyacrylamide gel electrophoresis (SDS-PAGE). Kinetic analysis of the enzymatic activity demonstrated apparent $K_m$ values of 18 $\mu$M and 22 $\mu$g/ml ($\sim$26 $\mu$M) for ATP and phosphatidylinositol (PtdIns), respectively. It has optimal activity in the pH range of about 6.0 to 7.0 and demonstrated a sigmoidal dependence of enzymatic activity or [Mg$^{++}$]. Ca$^{++}$ inhibited the enzyme at nonphysiological concentrations with about 50% inhibition observed at a free [Ca$^{++}$] of $\sim$ 300 $\mu$M. The enzyme utilized both ATP and 2'-deoxy-ATP as phosphoryl donors and specifically phosphorylated PtdIns on the 4-position. No PtdIns-4-P 5-kinase activity was present when the nucleotides ADP, GTP, ITP or CTP were used as phosphoryl donors.

PtdIns 4-kinase is a Mg$^{++}$-dependent, ATP utilizing lipid kinase. It has a broadly distributed membrane associated activity found in most tissues. Since PtdIns 4-kinase is the first ATP-utilizing enzyme in a highly divergent biosynthetic pathway involved in cell stimulation, cell growth, and possibly neoplastic transformation, its purification, isolation and characterization would have significant importance to medical science.

The PtdIns 4-kinase of the invention was isolated in a highly purified form which did not exist in the tissue from which it was initially obtained. That is, it has been prepared in a form which is essentially free of other proteins, and free from cellular components and tissue matter. In a representative example it was purified 10,148-fold to a specific activity of 2.7 $\mu$mol/mg/min. It constitutes the major PtdIns 4-kinase activity of bovine uteri. This purified enzyme exhibits biological activity which is deemed important to medical science in the study of the inositol-1,4,5- triphosphate and 1,2-diacylglycerol second messenger systems. The enzyme can be employed to cause phosphorylation or used as a basis upon which to develop antagonists to retard phosphorylation. It can be used to develop specific antibodies to study the relationship between two kinase activities found in bovine uteri and to determine the subcellular localization of each.

Detailed Description of the Invention

While the specification concludes with claims particularly pointing out and distinctly claiming the subject matter regarded as forming the present invention, It is believed that the invention will be better understood from the following detailed description taken in connection with the accompanying drawings in which, briefly:

FIG. 1 is a graphical representation of the elution profiles in the column chromatographic separation of PtdIns 4-kinase purified from bovine uterus in four representative runs shown as panels A, B, C and D as follows:

A. Column profile of Mono Q HR 16/10 step. This column was eluted at a flow rate of 2.0 ml/min. and 4.0 ml fractions were collected. B. Column profile of S-Sepharose Fast Flow step. The flow rate for this column was 2.0 ml/min. and the fraction size was 2.0 ml. C. Column profile of Mono Q HR 5/5 step. Elution was performed at a flow rate of 0.5 ml/min. and 0.5 ml fractins were collected. D. Column profile of Mono P chromatofocusing step. This column was eluted at a flow rate of 0.5 ml/min. and 0.5 ml fractions were collected.

Figure 1A:
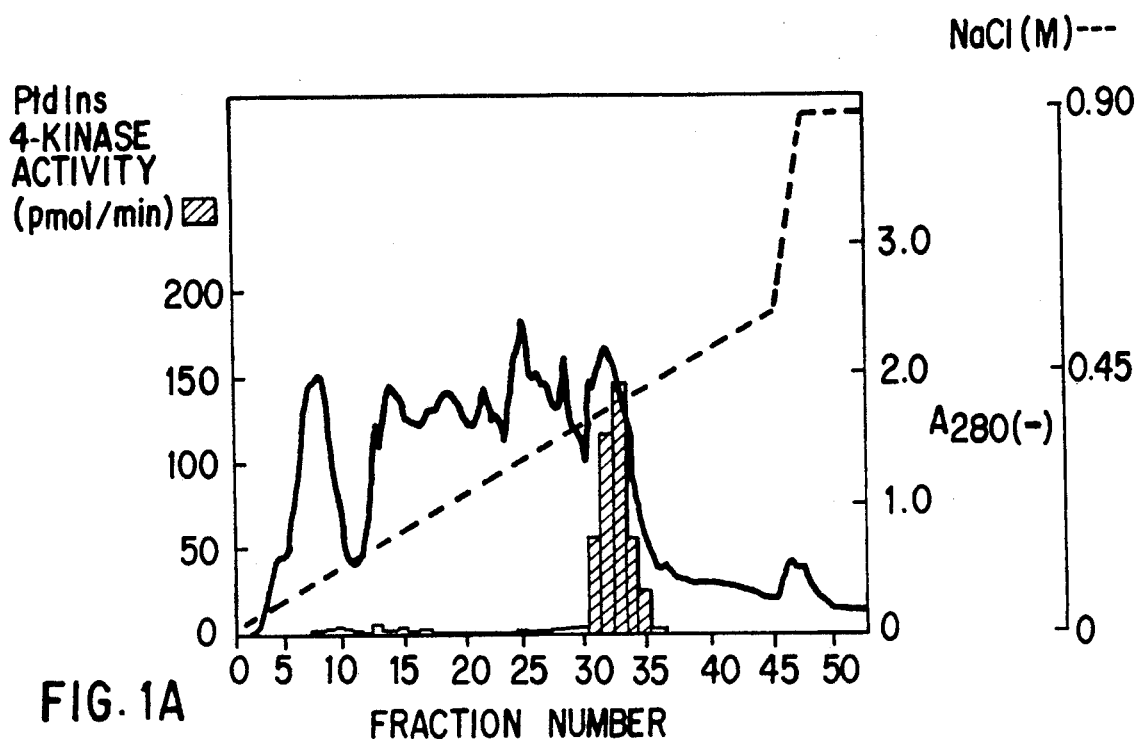
Figure 1B:
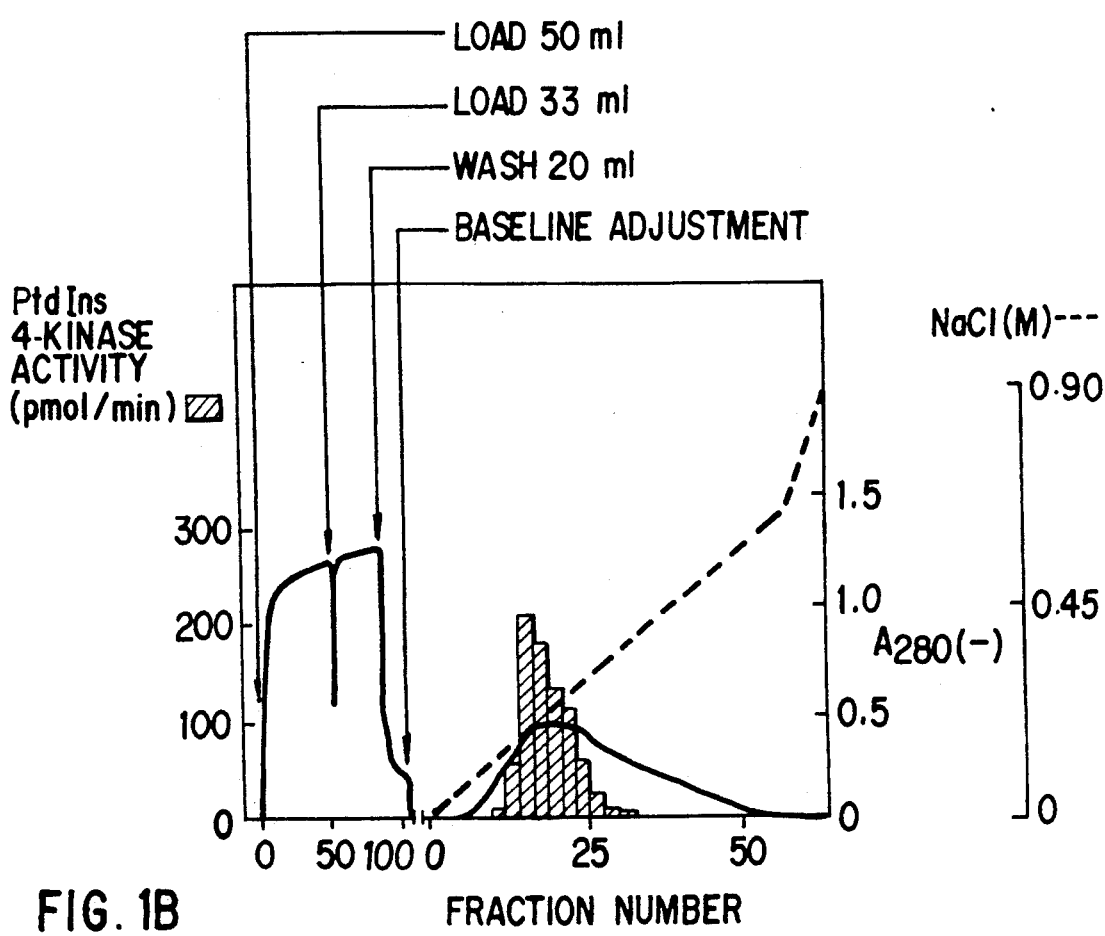
Figure 1C:
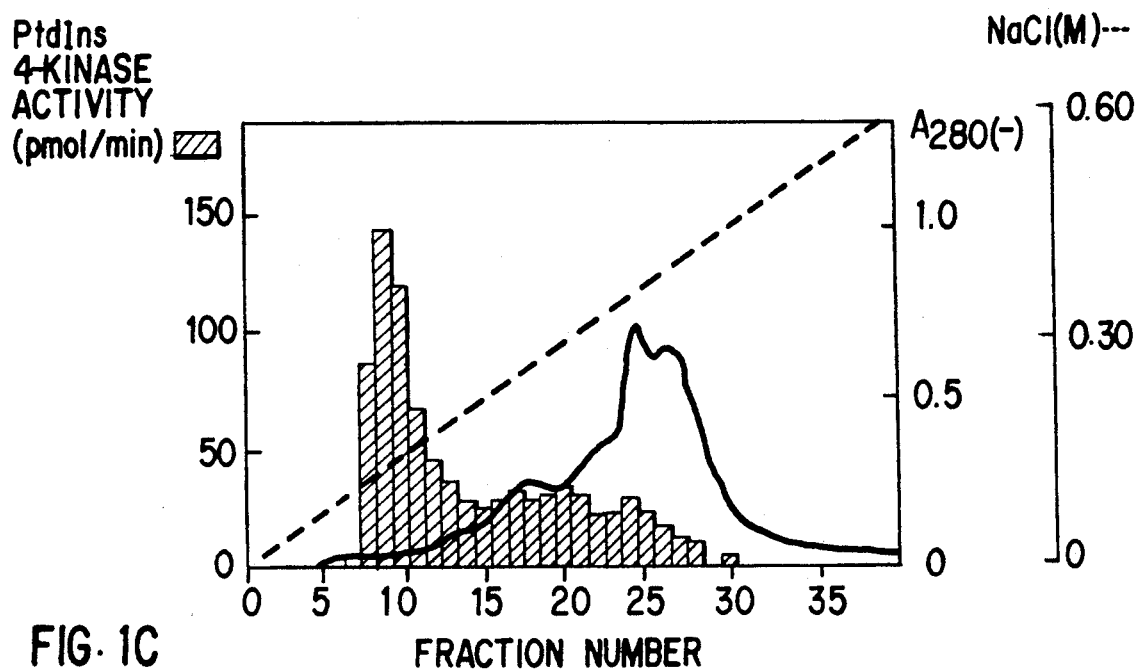
Figure 1D:
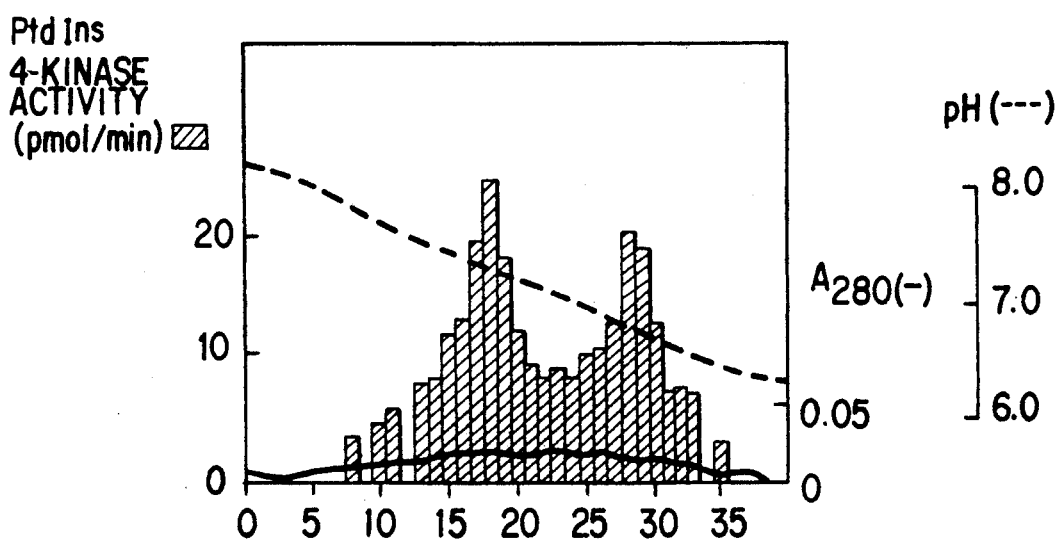

FIG. 2 shows the SDS-PAGE of the purified PtdIns 4-kinase following hydroxylapetite chromatography of peak fractions as in FIG. 1D. Panel A shows the silver-stained SDS-PAGE gel of the purified enzyme. Panel B shows the localization of PtdIns 4-kinase activity after SDS-PAGE. A representative example of the elution of PtdIns 4-kinase activity is shown.

FIG. 3 is a graphical representation which shows the ATP and PtdIns dependence of PtdIns 4-kinase activity. Panel A shows the dependence of PtdIns 4-kinase activity on increasing ATP concentrations. A double-reciprocal plot of the same data is shown in the inset. This assay was performed at a pH of 7.4 (Tris-HCl), and each data point represents the average of two assays. Panel B shows the dependence of PtdIns 4-kinase activity on increasing PtdIns concentrations. The inset is a double-reciprocal plot of the same data. This assay was performed at a pH of 7.0 (Tris-HCl), Triton X-

100/PtdIns ratios were maintained constant, and each data point represents the average of two assays.

Figure 4:
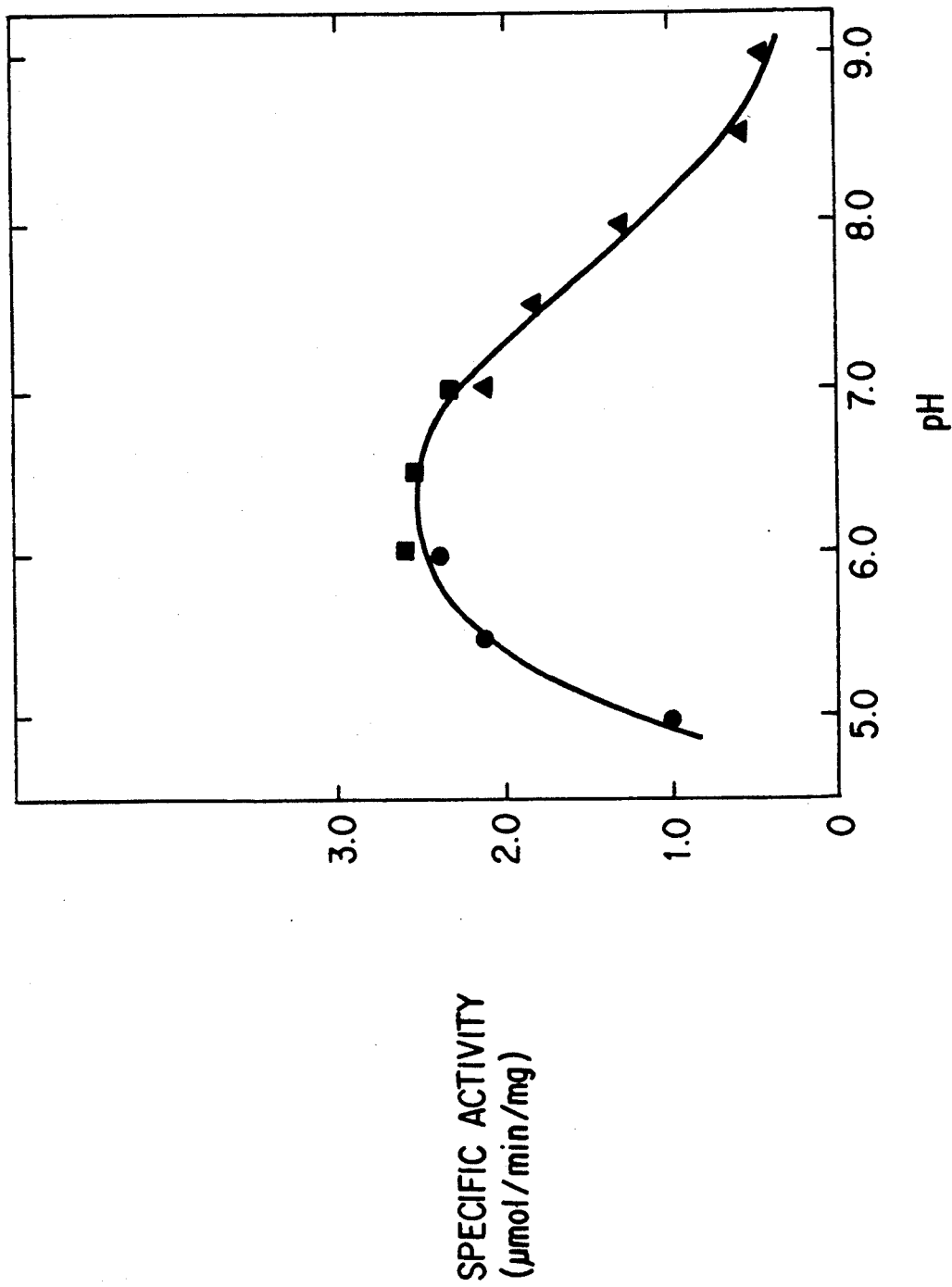

FIG. 4 is a graphical representation which shows the dependence of PtdIns 4-kinsase activity on pH. PtdIns 4-kinase activity was measured in assay media buffered with 50 mM sodium acetate-acetic acid ( , BisTris-HCl ( ), or Tris-HCl ( ) at the indicated pH as described hereinafter. Each data point represents the average of two assays.

Figure 5:
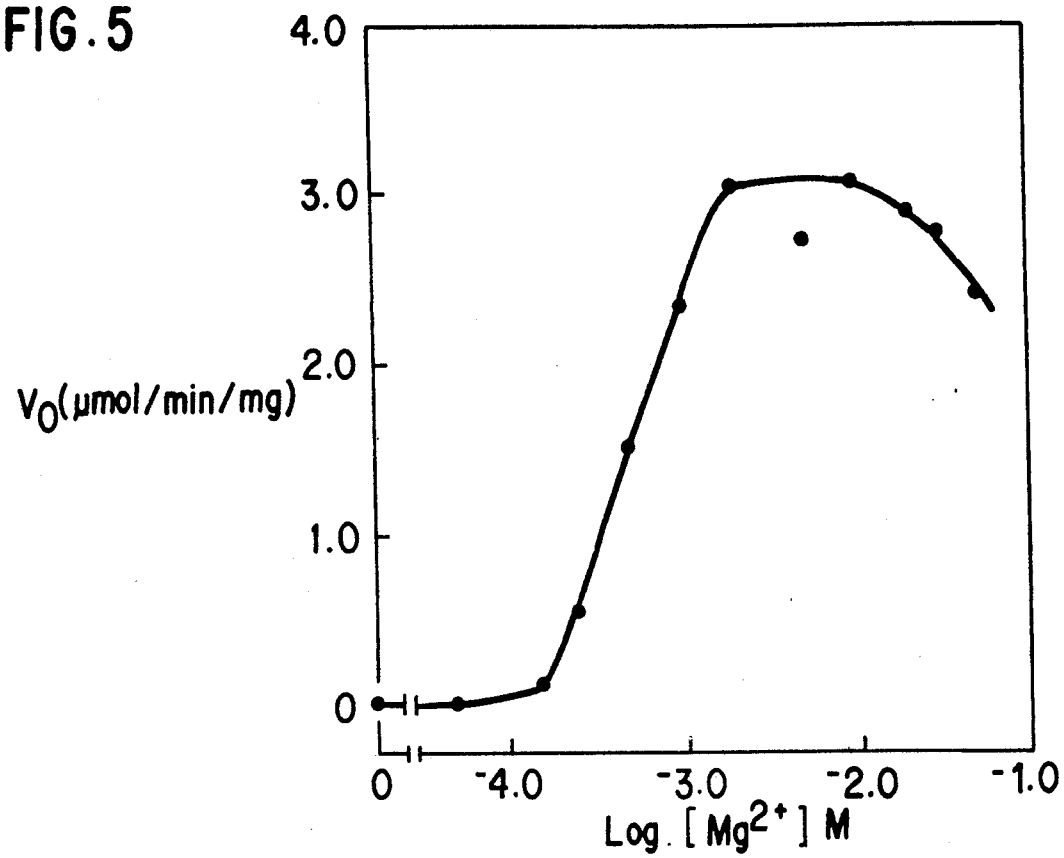

FIG. 5 is a graphical representation which shows $Mg^{2+}$ dependence of PtdIns 4-kinase activity. PtdIns 4-kinase activity was measured as described hereinafter except that the $[Mg^{2+}]$ was varied. Each data point represents the average of two assays.

Figure 6:
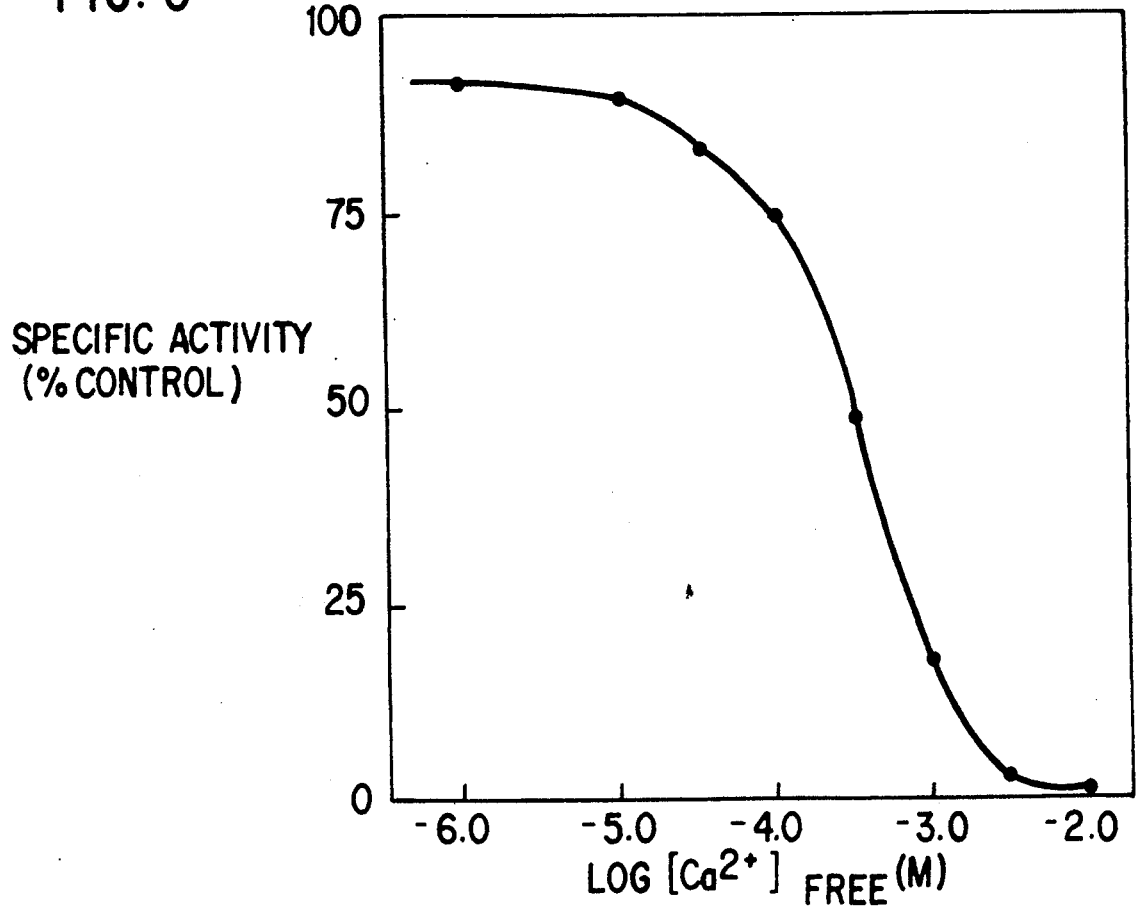

FIG. 6 is a graphical representation which shows the $Ca^{2+}$ inhibition of PtdIns 4-kinase activity. PtdIns 4-kinase activity was measured as described hereinafter except for the addition of 100 $\mu$M ATP and 100 $\mu$M EGTA. Calcium concentration was varied as indicated. Each data point represents the average of two assays. 100% is 2.7 $\mu$mol/mg/min.

The novel PtdIns 4-kinase enzyme of this invention differs from the PtdIns 4-kinase/PtdIns-4-P 5-kinase purified from bovine brain myelin by Saltiel et al., *Biochem. J.* 241, 759–763 (1987) and differs from the phosphoprotein identified by Kaplan et al., *Cell* 50, 1021–1029 (1987) and Courtneidge and Heber, *Cell* 50, 1031–1037 (1987) that correlates with a PtdIns 4-kinase activity. The enzymatic activity purified by Saltiel et al. from bovine brain myelin phosphorylated both PtdIns and PtdIns-4-P, exhibited a $K_m$ for PtdIns of 400 $\mu$M, had a specific activity of 0.028 $\mu$mol/mg/min, and its molecular mass was estimated to be 45 kDA. Kaplan et al. demonstrated that an 85 kDa phosphorprotein could be immunoprecipitated with antiphosphotyrosine antibodies from platelet-derived growth factor-treated cells, or from v-fms, v-sis, or polyoma-transformed cells. PtdIns 4-kinase activity showed a positive correlation with this 85 kDA phosphoprotein in the immunoprecipitates. Courtneidge and Heber identified an 81 kDa phosphoprotein in anti-middle T antigen and antipp60$^{C-arc}$ immunoprecipitates from polyoma virus-transformed cells. Importantly, this 81 kDa phosphoprotein and PtdIns 4-kinase activity were observed in immunoprecipitates from cells infected with transforming polyoma virus mutants, but not in immunoprecipitates from cells infected with nontransforming mutants. Based on these correlations, both these groups speculate that this 81–85 kDa phosphoprotein is a PtdIns 4-kinase; however, a definitive proof of this identity is lacking. In contrast, in accordance with the present invention there is purified to near homogeneity a 55 kDa PtdIns 4-kinase that is specific for PtdIns, had a specific activity of 2.7 $\mu$mol/mg/min, and a $K_m$ of approximately 26 $\mu$M for PtdIns. It is thus demonstrated that the invention provides a unique PtdIns 4-kinase activity that differs from those previously described.

The protein that has been purifed herein was identified as PtdIns 4-kinase using two criteria. First, the protein band that was identified as a PtdIns 4-kinase correlated directly with enzymatic activity on both chromatofocusing and hydroxylapatite chromatography. Second, enzymatic activity could be found to comigrate in SDS-PAGE gels with the silver-stained protein band. It also was established that the purified enzyme is specific for PtdIns and phosphorylates PtdIns on the fourth hydroxyl group of the inositol head group. This lipid kinase will utilize either ATP or 2-deoxy-ATP as a phosphoryl donor, and to a lesser degree will utilize 2,3-dideoxy-ATP. Kinetic characterization demonstrated apparent $K_m$ values of 18 $\mu$M and 22 $\mu$g/ml ($\sim$26 $\mu$M) for ATP and PtdIns, respectively.

Magnesium ions were required by this enzyme, with optimal activity observed at $Mg^{2+}$ between 2 and 10 mM, and the effect of $Mg^{2+}$ concentration on enzymatic activity could be modeled by the Hill equation with a Hill coefficient of 1.9, potentially indicating $Mg^{2+}$ binding sites. In contrast to the multimeric structure of most enzymes fitting an allosteric model, this enzyme in SDS-PAGE and gel permeation chromatography (4 mM deoxycholate and 0.1% deionized, reduced Triton X-100) appears to be monomeric, although it is possible in the assay buffer (1.0% Triton X-100) the enzyme may be present as a multimer due to different detergents conditions. However, although rare, monomeric enzymes that demonstrate allosteric interactions have been described by Panagou et al., *Biochemistry* 11, 2378–2388 (1972). Cytosolic free $Mg^{2+}$ concentrations have been estimated to be 0.37 mM by Corkey et al., *J. Biol. Chem.* 261, 2567–2574 (1986). Thus, the activity of this enzyme would be very sensitive to changes in $[Mg^{2+}]$; however, the concentration of $Mg^{2+}$ in cells is relatively stable. In contrast, $Ca^{2+}$ levels in cytoplasm are known to increase in response to mitogens, thus it is believed that an interaction of $Ca^{2+}$ and $Mg^{2+}$ may regulate the activity of this PtdIns 4-kinase.

Multiple PtdIns 4-kinase activities have been described. Harwood and Hawthorn, *Biochim. Biophys. Acta* 171, 75–88 (1969) reported differences between the PtdIns 4-kinase activities found in plasma membrane and microsomal preparations from rat livers. Recently, multiple forms of PtdIns 4-kinase activity have been described in bovine brain by Endermann et al., *Biochemistry* 26, 6845–6852 (1987), and mouse 3T3 fibroblasts by Whitman et al., *Biochem. J.* 247, 115–174 (1987) and *Nature* 332, 644–646 (1988). Bovine uteri has two distinct PtdIns 4-kinase activities which were readily separated. However, in the unpurified state, it is not possible to rule out that these apparent differences may be due to secondary effects on one enzyme. It is believed that there are multiple forms of PtdIns 4-kinase, and proposed that one enzyme might function in a signal transduction role, and the second enzyme might function in maintaining membrane structure.

In an illustrative embodiment of the invention, the PtdIns 4-kinase was isolated from bovine uteri in a series of steps comprising:
  (a) homogenizing bovine uteri;
  (b) acetone extracting the resulting homogenate;
  (c) concentrating the acetone extracted material by ammonium sulfate precipitation;
  (d) subjecting the resulting concentrated fractions to a sequence of ion exchange chromatographic separations with Mono Q, S-Sepharose and then Mono Q ion exchange resins;
  (c) subjecting the resulting active fractions to chromatofocusing with Mono P Polybuffer exchanger;
  (f) subjecting the resulting active fractions to hydroxylapetite chromatography; and
  (g) recovering the resulting active PtdIns 4-kinase.

In the foregoing method, the chromatographic materials are all available commercially. Thus, Mono Q is a strong anion exchange resin based on a hydrophilic polymer in bead form, diameter about 10 μM, with quaternary amino charged groups.

S-Sepharose is a fast flow, strong anion exchanger based on cross-linked agarose gel Sepharose.

Mono P is a Polybuffer exchanger (PBE) which is a bead formed anion exchanger gel used with Polybuffers, both of which are used for chromatofocusing.

Mono Q, Mono P and S-Sepharose are all available from Pharmacia, Piscataway, N.J.

Hydroxylapetite is a calcium gel available from Bio-Rad, Richmond, Calif.

Although particular methods of isolating the PtdIns 4-kinase are described herein, it will be understood that the novel PtdIns 4-kinase is not limited to any specific method of preparation.

In order to illustrate specific preferred embodiments of the invention in greater detail, the following exemplary laboratory preparative work was carried out.

Example

Materials

Mature bovine uteri were obtained from Pel-Freeze (Rogers, AR). Silica Gel 60 thin layer chromatography plates (0.25 mm layer thickness) were from Whatman. Solvents (reagent grade) were obtained from Mallinkrodt Chemical Works. Phosphatidylinositol (soybean, bovine), L-α-phosphatidylinositol 4-monophosphate, L-α-phosphatidylinositol 4,5-diphosphate, L-α-lysophosphatidylinositol, L-α-phosphatidylcholine, L-α-phosphatidyl-L-serine, L-α-phosphatidylethanolamine, glucocerebrosides, and galactocerebrosides (mixed) deoxycholate, Triton® X-100, and protease inhibitors were from Sigma. Octyl-β-D-glucopyranoside was from Behring Diagnostics, reduced Trion X-100 was from Aldrich, and ammonium sulfate (ultrapure) was from Schwarz/Mann. Nucleotides were from Pharmacia LKB Biotechnology Inc. [γ-$^{32}$P]ATP and L-α-[myo-inositol-2-$^3$H]phosphatidylinositol were from DuPont-New England Nuclear. Pharmacia FPLC Equipment, Mono Q and Mono P columns, Polybuffers and S-Sepharose® Fast Flow were used from chromatography. Hydroxylapatite chromatography was performed on a Bio-Rad Bio-Gel® HPHT column. All other reagents were analytical grade.

Preparation of Acetone Powders

Frozen mature bovine uteri were shredded using a Hobart "HOGO" vegetable shredder. Approximately 200 g of shredded uteri were reduced to powder with dry ice in a Waring blendor, homogenized with 250 ml of acetone (−20° C.) for 3 min. rapidly vaccum-filtered on a Buchner funnel, washed with approximately 2 liters of acetone (−20° C.), collected, and rehomogenized with 250 ml of acetone for 3 min. This homogenate was filtered and washed as above. The acetone powder was collected, dried under vacuum, and stored at −20° C. The enzymatic activity of the acetone powders was stable for more than 6 months. Comparison of uterine extracts with solubilized acetone powders suggested nearly complete recovery of PtdIns 4-kinase activity.

Extraction of PtdIns 4-Kinase from Acetone Powders

The acetone powders were first extracted with 40 ml/g of 0.9 M NaCl, 20 mM Tris-HCl (pH 8.0), 5 mM [ethyleneglycolbis(β-aminoethyl ether)tetraacetic acid](EGTA), 0.15 mg/ml phenylmethylsulfonyl fluoride, 10 mM benzamidine, 0.1 mg/ml soybean trypsin inhibitor, and 1 μg/ml aprotinin for 2 h at 4° C. with agitation, and then centrifuged at 10,000 ×g for 30 min. The pellet was washed with 50 mM NaCl, 20 mM Tris-HCl (pH 8.0), and 5 mM EGTA (20 ml/g starting material). The wash was completed by centrifugation at 10,000 ×g for 15 min. The supernatant was discarded, and the pellet was reextracted with 20 ml/g starting material (50 mM NaCl, 20 mM Tris-HCl, pH 8.0), 5 mM EGTA, 0.15 mg/ml phenylmethylsulfonyl fluoride, 10 mM benzamidine, 0.1 mg/ml soybean trypsin inhibitor, 1 μg/ml phenylmethylsulfonyl fluoride, 10 mM benzamidine, 0.1 mg/ml soybean trypsin inhibitor, 1 μg/ml aprotinin, and 40 mM octyl-β-D-glucopyranoside (octylglucoside) for 2 h at 4° C. with agitation, and then centrifuged for 60 min at 10,000 × g. The supernatant was collected, frozen with liquid nitrogen, and stored at −70° C.

Assay of PtdIns 4-Kinase Activity

PtdIns 4-kinase activity was assayed in 60 μl at 30° C. in 20 mM BisTris-HCl (pH 7.0), 10 mM MgCl$_2$, 1.0% Triton X-100, 0.25 mg/ml phosphatidylinositol, and 150 μM ATP (1.25 μCi[-$^{32}$P]ATP), unless otherwise noted. The reaction was terminated by the addition of 12 μl of cold HCl, 120 μl of cold methanol, 150 μl of chloroform, and 40 μl of H$_2$O. The extracted samples were centrifuged at 12,000 × g for 1 min. and the aqueous layer removed and discarded. When needed, the organic phase was washed with 40 μl of cold methanol and 40 μl of cold 1.0 N HCl, centrifuged at 12,000 × g, and the aqueous layer was removed. The organic phase was then dried under vacuum in a Savant speed-vac, resuspended in 40 μl of chloroform/methanol (2:1), and chromatographed on potassium oxalate-impregnated Silica Gel 60 thin layer chromatography plates (TLC). The solvent system used consisted of chloroform/methanol/ammonium hydroxide/water (51:39.6:3:8.4). For two-dimensional thin layer chromatography, the preceding solvent system was used for the first dimension, and chloroform/methanol/acetic acid/water (50:39:1:10) was used for the second dimension. Standards were visualized by exposing the TLC plate to iodine vapor. The reaction product, phosphatidylinositol 4-phosphate, was visualized by autoradiography, and the corresponding area of the TLC plate was scraped and quantitated by Cherenkov counting. This assay was linear with respect to both protein concentration and time. For tests utilizing [$^3$H]PtdIns, the corresponding areas of the TLC plates were scraped and the silica powder was suspended in a gel of Aquasol/H$_2$O (4:1) before counting. All assays (except column fractions) were done in duplicate or triplicate.

Purification of PtdIns 4-Kinase

Powdered ammonium sulfate was added slowly to the extracted enzyme to a final concentration of 295 g/liter of extract (∼47.5% saturation), stirred for 1 h at 4° C., and centrifuged at 10,000 × g for 60 min. The supernatant was discarded, and the pellet was resuspended in 0.2 volume of 20 mM NaCl, 20 mM Tris-HCl (pH 8.0), and 1 μg/ml aprotinin, and dialyzed against this buffer. The dialyzed enzyme was centrifuged at 10,000 × g for 1 h, frozen in liquid nitrogen, and stored at −70° C. for subsequent purification.

The ammonium sulfate-precipitated activity was made 4 mM deoxycholate, 10 mM octylguoside, stirred for 1 h, loaded onto a Pharmacia HR 16/10 Mono Q column previously equilibrated with 20 mM NaCl, 20 mM Tris-HCl (pH 8.0), 0.1% deionized (by passage of a 10% v/v solution over Amberlite® MB-1), reduced Triton X-100, and 1 mM dithiothreitol (DTT), and washed with 25 ml of equilibration buffer. The elution buffer was Composed of 900 mM NaCl, 20 mM Tris-HCl (pH 8.0), 0.1% deionized, reduced Triton X-100, and 1 mM DTT. The column was eluted with a 180 ml 0–60% linear gradient of equilibration to elution buffer, followed by a 10 ml 60–100% linear gradient. The column fractions were assayed, and the active fractions were frozen and stored at $-70°$ C.

Active fractions from multiple runs of the HR 16/10 Mono Q column were combined and first dialyzed against 50 mM NaCl, 20 mM BisTris-HCl (pH 7.0), 0.1% deionized, reduced Triton X-100, and 1 mM DTT and then dialyzed against 50 mM NaCl, 20 mM BisTris-HCl (pH 6.0), 0.1% deionized, reduced Triton X-100, and 1 mM DTT. After Centrifugation the dialyzed preparation was then chromatographed using a 7 ml column of S-Sepharose Fast Flow, Equilibrated with 50 mM NaCl, 20 mM BisTris-HCl (pH 6.0), 0.1% deionized, reduced Triton X-100, and 1 mM DTT. The column was washed with 20 ml of equilibration buffer. The elution buffer was Composed of 900 mM NaCl, 20 mM BisTris-HCl (pH 6.0), 0.1% deionized, reduced Triton X-100, and 1 mM DTT. The column was eluted with a 50 ml 0–70% linear gradient of equilibrium to elution buffers followed by a 5 ml 70–100% linear gradient. Column fractions were assayed and active fractions combined for dialysis against 20 mM NaCl, 20 mM Tris-HCl (pH 8.0), 0.1% deionized, reduced Triton X-100, 100 $\mu$M deoxycholate, and 1 mM DTT. The fractions were then loaded onto a Pharmacia HR 5/5 Mono Q column equilibrated with 20 mM NaCl, 20 mM Tris-HCl (pH 8.0), 0.1% deionized, reduced Triton X-100, 100 $\mu$M deoxycholate, and 1 mM DTT, washed with equilibration buffer and eluted with a 30 ml 0–100% linear gradient of equilibrium buffer to elution buffer. The elution buffer was composed of 900 mM NaCl, 20 mM Tris-HCl (pH 8.0), 0.1% deionized, reduced Triton X-100, 100 $\mu$M deoxycholate, and 1 mM DTT. Column fractions were assayed for activity, and active fractions were pooled.

The active fractions from the second Mono Q column were dialyzed against 10 mM NaCl, 25 mM triethanolamine (pH 8.3), 10% Betaine (w/v), and 0.1% deionized, reduced Triton X-100, loaded onto a Pharmacia MonoP chromatofocusing column equilibrated with the above buffer, washed until the effluent pH stabilized at pH 8.3, and eluted with 50 mL of 10 mM NaC, 7.0% Polybuffer 74/3.0% Polybuffer 96 (pH 5.0), 10% Betaine, and 0.1% deionized, reduced Triton X-100. The pH gradient was monitored using a flow-through pH electrode. The column fractions were assayed for activity, and active fractions were frozen and stored at $-70°$ C.

The active fractions from the chromatofocusing step were pooled and dialyzed against 10 mM sodium phosphate (pH 7.5), 0.1% deionized, reduced Triton X-100, 1 mM DTT, and 100 $\mu$M deoxycholate. The sample was then loaded onto a Bio-Rad Bio-Gel HPHT column (100×7.8 mm), equilibrated with 10 mM sodium phosphate (pH 7.5), 0.1% deionized, reduced Triton X-100, 1 mM DTT, and 100 $\mu$M deoxycholate. The column was washed with 10 ml of equilibration buffer, and eluted with a 40 ml linear gradient between equilibration buffer and 350 mM sodium phosphate (pH 7.5), 0.1% deionized, reduced Triton X-100, 1 mM DTT, and 100 $\mu$M deoxycholate. Column fractions were assayed for activity, active fractions were frozen in liquid nitrogen and stored at $-70°$ C. In some preparations, a 25–30 kDa contaminate was not completely removed by this step. Removal of this contaminate could be achieved by concentrating the active fractions in an Amicon spin concentrator (P-30) and utilizing gel permeation chromatography. A Pharmacia Superose-12 column was used with a buffer composed of 150 mM NaCl, 50 mM sodium phosphate (pH 7.5), 0.1% deionized, reduced Triton X-100, 4 mM phosphate (pH 7.5), 0.1% deionized, reduced Triton X-100, 4 mM deoxycholate, 1 mM DTT.

SDS-PAGE

Discontinuous polyacrylamide gel electrophoresis (PAGE) was performed on Hoffer minigel apparatus. Protein bands and molecular weight standards were localized by silver staining. For localization of enzymatic activity, the enzyme preparation was loaded on a 10% minigel in 62 mM Tris-HCl (pH 6.8), 3% SDS, 2 mM DTT, and 10% v/v glycerol as described by Saltiel et al., *Biochem. J.* 241, 759–763 (1987). One lane of the gel was sliced into 2 mm sections which were homogenized in 100 $\mu$l of assay media. The enzymatic activity was extracted at 4° C. for 12-14 h. Polyacrylamide gel fragments were removed by centrifugation. The supernatant was tested for PtdIns 4-kinase activity by the addition of [$\gamma$-$^{32}$P]ATP (20 $\mu$M) and incubation at 30° C. for 30 min. Analysis of the reactions was as described above. Adjacent lanes were silver-stained and prestained standards were used to extablish the positions of the gel slices.

Other Techniques

Free calcium concentrations were established as described by Barfai, *Adv. Cyclic Nucleotide Res.* 10, 219–242 (1979). Phospholipase C cleavage of PtdIns-4-P and identification of the resulting inositol phosphates were performed in a manner similar to that described by Majerus and co-workers, *J. Biol. Chem.* 262, 15946–15952 (1987); *Ibid.*, 257, 6461–6469 (1982); *Ibid.*, 259, 11717–11724 (1984); and *Proc. Natl. Acad. Sci. U.S.A.* 84, 1206–1209 (1987). Protein concentrations were determined using the Bio-Rad dye binding assay using bovine serum albumin as a standard protein. Purified enzyme concentrations were estimated by comparing silver-stained bands of titrated standards with silver stained bands of PtdIns 4-kinase.

Results

Purification of PtdIns 4-kinase

PtdIns 4-kinase was purified from bovine uteri to near homogeneity as outlined above. A representative purification of PtdIns 4-kinase is outlined in Table I. Marked instability of the kinase activity and the tendency of this enzyme to aggregate complicated purification and resulted consistently in poor yields. Although the detergene-extracted enzyme remained in solution after removal of the octylglucoside, it was localized to the void volume of a Pharmacia Superose-6 gel permeation column (data not shown) and thus apparently was present in large aggregates. Anion exchange chromatography without detergents was not possible because the activity smeared across most of the protein-containing fractions. Using anion exchange chromatography, various detergents were tested for their ability to disaggregate the PtdIns 4-kinase activity. Octylglucoside (15 and 40 mM), Lubrol PX (0.1%), and CHAPS (10 mM) were ineffective; octylglucoside (10 mM) plus CHAPS (10 mM) were partially effective, whereas the combination of octylglucoside (20 mM) plus deoxycholate (4 mM) resulted in the elution of a sharp activity peak. Gel permeation chromatography confirmed that octylgluoside (10 mM) plus deoxycholate (4 mM) disaggregated PtdIns 4-kinase activity (data not shown).

TABLE 1

Purification of PtdIns 4-kinase

| Step | Volume ml | Protein mg/ml | Specific activity nmol/mg/min | Total activity nmol/min | Yield % | Purification fold |
|---|---|---|---|---|---|---|
| 1. Acetone powder extract | 3,800 | 0.70 | 0.27 | 718 | 100 | |
| 2. NH$_4$SO$_4$ precipitation | 660 | 0.28 | 0.62 | 524 | 73 | 2 |
| 3. MonoQ | 66 | 1.20 | 3.14 | 248 | 35 | 12 |
| 4. S-Sepharose fast flow | 10 | 0.57 | 12.3 | 70 | 10 | 46 |
| 5. MonoQ | 2 | 0.22 | 49.3 | 23 | 3.2 | 183 |
| 6. MonoP | 14.1 | $1.0.10^{-3}$ | 294 | 4.1 | 0.6 | 1,089 |
| 7. HPHT | 0.5 | $1.3.10^{-4}$ | 2,740 | 0.2 | $3.10^{-2}$ | 10,148 |

Ammonium sulfate precipitation was utilized to concentrate the extracted material and to improve the purification obtained in the subsequent step. Anion exchange chromatography in octylglucoside (10 mM) and deoxycholate (4 mM) was important to the purification. FIG. 1A shows a representative column profile in which most of the PtdIns 4-kinase activity eluted late (fraction 30-30) in the NaCl gradient. However, under slightly different conditions, PtdIns 4-kinase activity eluted substantially earlier (near fraction 10). The factor determining the position of elution appeared to be whether significant amounts of deoxycholate bound to the enzyme (high salt elution) or not (low salt elution). Pretreatment of the enzyme with detergents, the size of the column, and the washing of this column were important factors. After dialysis to pH 6.0, cation exchange chromatography on S-Sepharose Fast Flow was used to purify this enzyme further (FIG. 1B). Subsequent anion exchange chromatography of the active fractions from the previous step that had been dialyzed to 100 μM deoxycholate and pH 8.0 is shown in FIG. 1C. This column is required to remove a major protein contaminate that cochromatographed with PtdIns 4-kinase subsequently. Chromatofocusing on a Pharmacia MonoP column was next utilized to purify this enzyme (FIG. 1D). Although recovery of enzymatic activity was poor, this step was used to purify this enzyme because exhaustive attempts with other methods were ineffective. Two peaks of Ptdlns kinase activity are observed at ~pH 7.2 (basic form), and at ~pH of 6.7 (acidic form). For reasons not understood, the peak ratio of the two was variable from batch to batch and run to run. Silver staining of SDS-PAGE gels of those column fractions identified a 55 kDa protein band in both peaks whose intensity directly correlated with enzymatic activity.

Figures 2A, 2B:
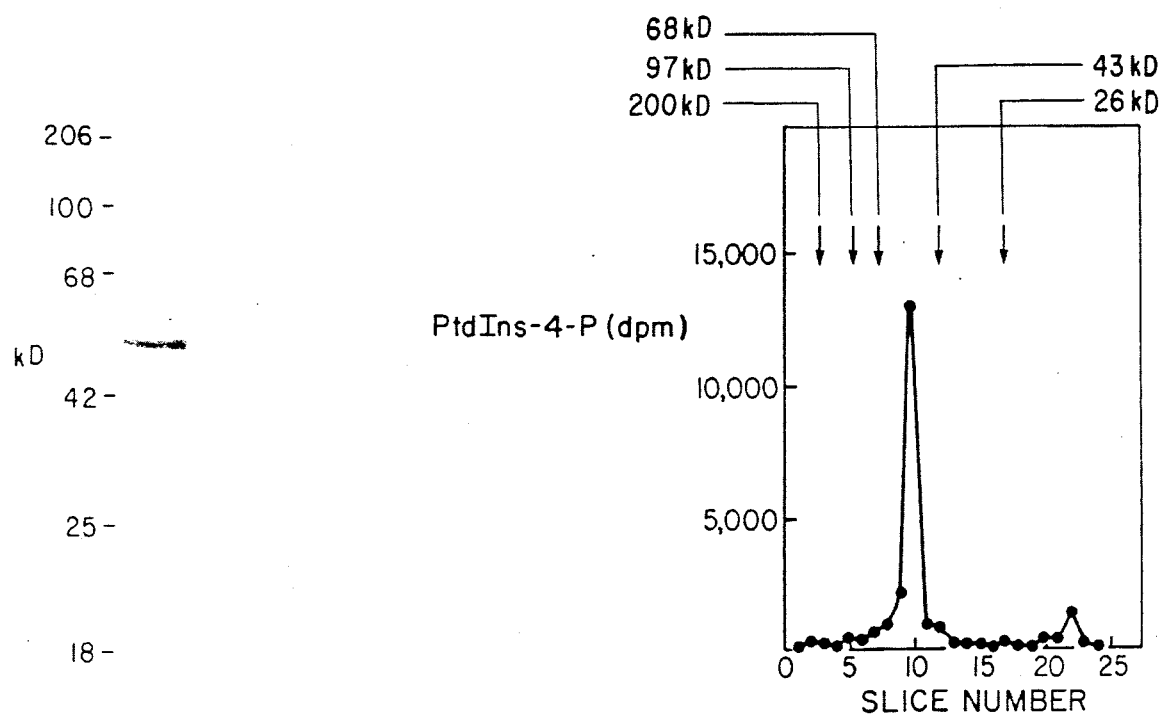

Hydroxylapatite chromatography was then used to remove remaining contaminating proteins and Polybuffer. This step yielded a nearly homogeneous enzyme preparation with an estimated specific activity of 2.7 μmol/mg/min. Silver-stained SDS-PAGE gels of column fractions demonstrated a single 55 kDa protein band (FIG. 2A) which directly correlated with enzymatic activity (data not shown). FIG. 2B demonstrated that the 55 kDa region of these gels contained extractable PtdIns 4-kinase activity. In these tests, one lane of the gel was sliced into 2 mm sections, homogenized, and extracted in assay bufffer and then assayed for PtdIns 4-kinase activity. An adjacent lane was silver-stained. Prestained standards were used to localize the gel slices. The peak of PtdIns 4-kinase activity was in the same slice of gel that contained the 55 kDa protein band. Recovery of enzymatic activity was about 1-5% in several separate tests. When material concentrated by ammonium sulfate (step 1) was separated by SDS-PAGE, PtdIns 4-kinase activity was recovered from the same region of the gel as was observed with the purified enzyme, suggesting that comigration of the enzymatic activity with this 55 kDa major protein band was probably not due to aggregation of PtdIns 4-kinase with other proteins. Both the acidic and basic peaks from the chromatofocusing step had activity at 55 kDa.

Identification of the Enzymatic Product

The identity of the $^{32}$P-labeled product of this enzymatic activity as PtdIns-4-P was established using several criteria. First, the $^{32}$P-labeled product comigrated with authentic PtdIns-4-P in both one-dimensional and two-dimensional thin layer chromatography systems (data not shown). Second, after elution of this $^{32}$P-labeled molecule from thin layer chromatography plates, it was incorporated into liposomes and treated with a phosphoinositide-specific phospholipase C [Hoffmann and Majerus, *J. Biol. Chem.* 257, 6461–6469 (1982) and Wilson et al., *Ibid.* 259, 11717–11724 (1984)]which degrades PtdIns-4 P to yield 1,2-diacylglycerol and Ins-1,4-P$_2$. 88% of the label was found to partition into an aqueous phase, as would be expected of Ins-1,4-P$_2$. Finally, the water-soluble product of the phospholipase C reaction coeluted as a single peak with authentic Ins-1,4-P$_2$ when chromatographed on a Partisil SAX dolumn Auohus et al., *Proc. Natl. Acad. Sci. U.S.A.* 84, 1206–1209 (1987)]. It was established that this enzyme, as predicted, adds a phosphate to the fourth hydroxyl of the inositol head group of PtdIns. The putative Ins-1,4-P$_2$ isolated from Partisil SAX chromatography was treated with an Ins-1,4-P$_2$ specific 1-phosphatase Inhorn and Majerus, *J. Biol. Chem.* 262, 15946–15952 (1987)]. Subsequent chromatography, as described above, demonstrated that the putative Ins-1,4-P$_2$ was converted to Ins-4-P, establishing that the enzymatic activity that was purified phosphorylates PtdIns to form PtdIns-4-P.

Characterization of the Purified PtdIns Kinase

Figure 3A:
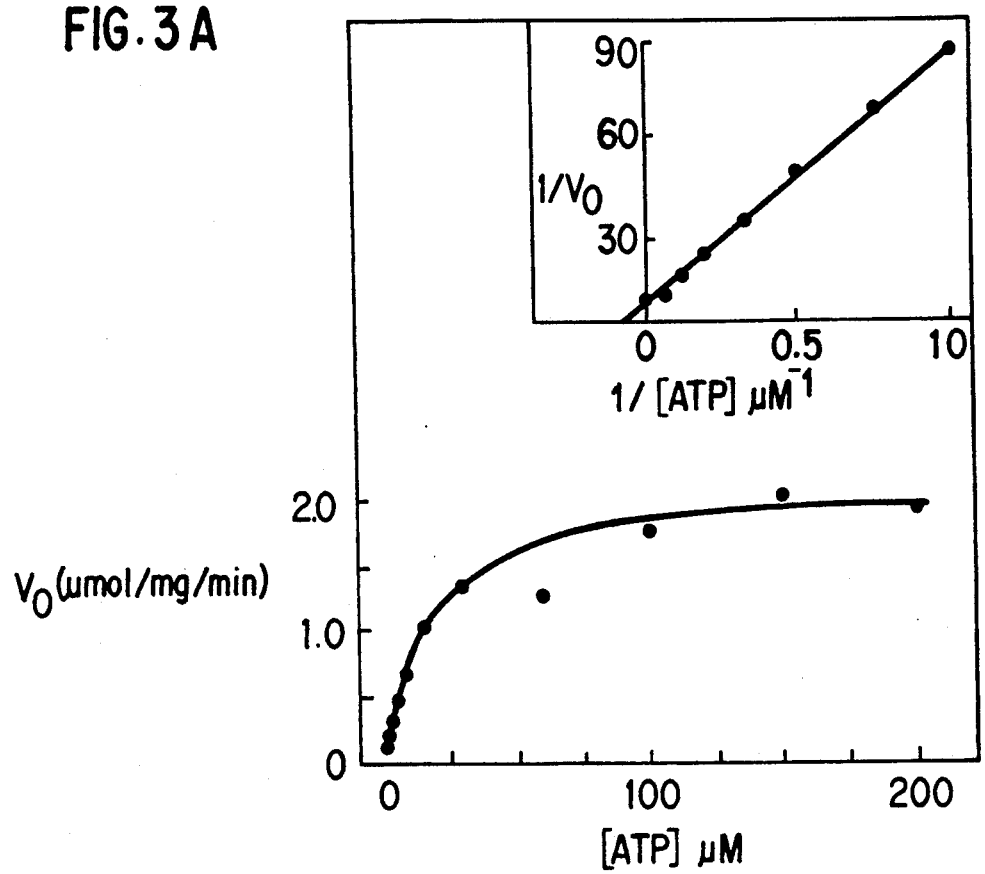
Figure 3B:
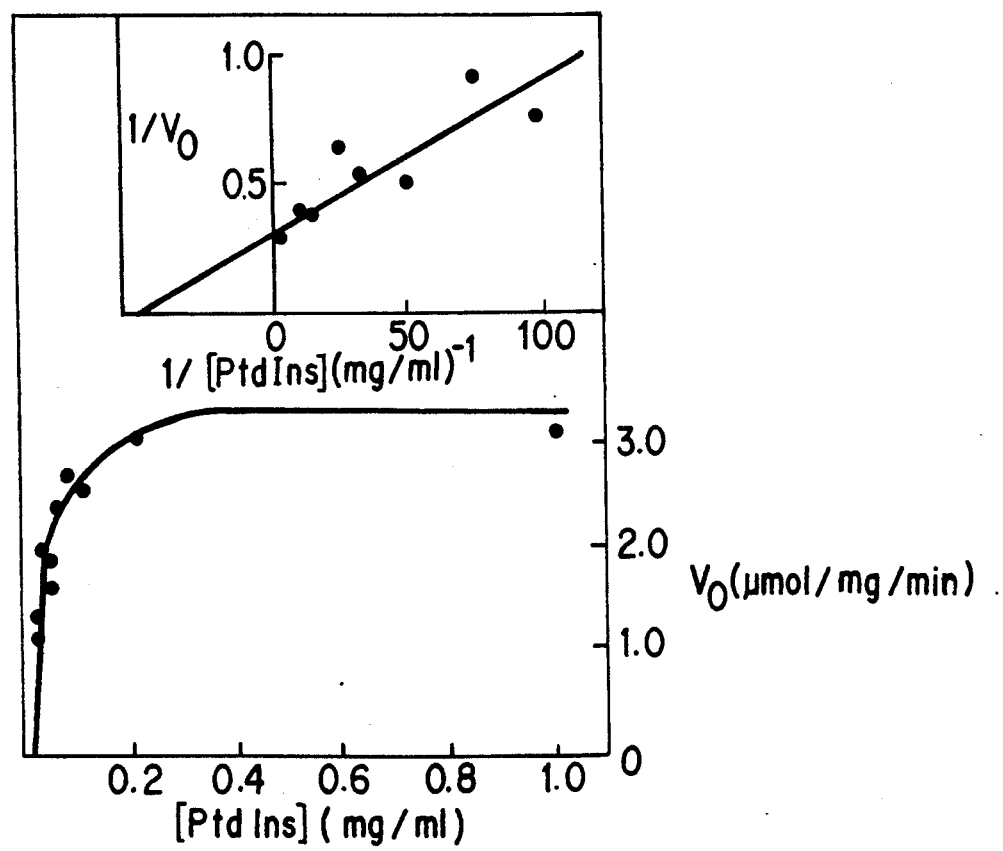

The purified PtdIns 4-kinase was used to determine the kinetic parameters of this enzyme for ATP and PtdIns. The effects of increasing ATP concentrations on activity are shown in FIG. 3A. Optimal enzymatic activity was found at concentrations of ATP above 100 μM. Analysis of a linear double-reciprocal plot of these data revealed an apparent $K_m$ of 18 $\mu$M and a $V_{max}$ of 2.2 $\mu$mol/mg/min. The effects of increasing PtdIns concentrations on PtdIns kinase activity are shown in FIG. 3B. In order to avoid potential effects on enzymatic activity due to changes in the Triton X-100/PtdIns micelles used as substrate, a constant molar ratio of Triton X-100 to PtdIns was used, and the concentration of Triton X-100 was maintained above its critical micellar concentration. Saturation of enzyme activity was observed at concentrations of PtdIns above 0.2 mg/ml. Analysis of the linear double-reciprocal plot yielded an apparent $K_m$ of 22 $\mu$g/ml (26 $\mu$M assuming a molecular weight of 835.2 for PtdIns) and a $V_{max}$ of 3.3 $\mu$mol/mg/min. The different $V_{max}$ values may be explained by the fact that the ATP substrate saturation curve was performed at a pH of 7.4 rather than 7.0.

In order to optimize the assay of this enzyme, the pH optimum for PtdIns 4-kinase was determined. This enzyme was optimally active in the pH range of 6.0–7.0 (FIG. 4). Above a pH of 7.0 and below a pH of 6.0 the activity of this enzyme decreased sharply.

The influence of divalent cations on PtdIns 4-kinase activity was studied as one possible mechanism for its regulation. FIG. 5 demonstrates activation of this enzyme by $Mg^{2+}$ Maximum activity was observed at $Mg^{2+}$ concentrations between 2 and 10 mM, concentrations of $Mg^{2+}$ much higher than needed to saturate the ATP (150 $\mu$M) present in the reaction. Analysis of these data using a nonlinear regression curve-fitting program (Enzfitter, Elsevier-BIOSOFT) demonstrated that these results could be modeled by the Hill equation with a Hill coefficient of 1.9 and a $K_s$ of 0.36, suggesting that the enzyme may have $Mg^{2+}$ binding sites that allosterically regulate the activity of the enzyme.

One consequence of cellular activation by growth factors is a transient increase in cytoplasmic calcium concentrations from approximately 200 nM to approximately 1 $\mu$M, suggesting that PtdIns 4-kinase activity might be regulated directly by this increase. FIG. 6 demonstrates the effect of increasing the free calcium concentrations on the activity of this enzyme. PtdIns kinase activity is inhibited by $Ca^{2+}$. 50% inhibition was observed at approximately 300 $\mu$M free $Ca^{2+}$, a concentration of $Ca^{2+}$ well above the physiological levels found in cells. Increasing $Mg^{2+}$ concentrations antagonize this inhibition $Ca^{2+}$ (data not shown).

The specificity of PtdIns 4-kinase for nucleotide phosphoryl donors was tested using [$^3$H]PtdIns as substrate (Table 11). ATP and 2-deoxy-ATP were both utilized by PtdIns 4-kinase to synthesize PtdIns-4-P. 2,3-Dideoxy-ATP was partially effective. A small amount of PtdIns-4-P was observed when UTP was used as a phosphoryl donor. No PtdIns-4-P was observed when ADP, GTP, ITP, or CTP were used as phosphoryl donors. Thin layer chromatography (PEI cellulose, 1,6 M LiCl) demonstrated only a single nucleotide in each preparation, and demonstrated no detectable contamination of the UTP with ATP.

TABLE 11

Specificity of PtdIns 4-kinase for a nucleotide phosphoryl donor

| Nucleotide donor a (150 $\mu$M) | (n) | Relative activity |
|---|---|---|
| ATP | (6) | 100 |
| ADP | (6) | 12 |
| dATP | (6) | 104 |
| ddATP | (3) | 39 |
| ITP | (6) | 11 |
| GTP | (6) | 5 |

TABLE 11-continued

Specificity of PtdIns 4-kinase for a nucleotide phosphoryl donor

| Nucleotide donor (150 $\mu$M) | (n) | Relative activity |
|---|---|---|
| CTP | (6) | 10 |
| UTP | (6) | 18 |
| TTP | (3) | 3 |

The specificity of PtdIns 4-kinase for lipid substrates was also examined using standard assay buffer containing 0.25 mg/mg of the indicated lipid. After extraction the organic phase was washed three times, dried in vacuo, and the organic extractable label was quantitated. Control reactions (no lipid) established background levels which were then subtracted from the experimentally derived values (Table III). The purified enzyme was able to phosphorylate PtdIns derived from soybean (primarily 1-palmitoyl-2-linoleoyl) or bovine brain (primarily 1-stearoyl-2-arachidonoyl). The sensitivity of the above technique was limited and appeared to show little or no activity with lyso-PtdIns; however, subsequent TLC of these reactions established that the enzyme would phosphorylate lyso-PtdIns about 10% as well as soybean PtdIns. The enzyme preparation lacked detectable PtdIns-4-P 5-kinase activity nor would it phosphorylate PtdIns-4,5-P$_2$. It also lacked diacylglycerol kinase activity and would not phosphorylate other lipids, such as galactocerebrosides or glucocerebrosides, which contain free hydroxyl groups on six-membered rings. In addition, no phosphorylation of phosphatidylcholine, phosphatidylethanolamine, or phosphatidylserine was observed. Except for lyso-PtdIns, the results presented in Table III were confirmed by thin layer chromatography.

TABLE III

Specificity of PtdIns 4-kinase for a lipid substrate

| Lipid added (0.25 mg/ml) | Relative activity % |
|---|---|
| PtdIns (soybean)$^a$ | 100 |
| PtdIns (bovine)$^b$ | 110 |
| Lyso-PtdIns | 0 |
| PtdIns-4-P | 0 |
| PtdIns-4,5-P$_2$ | 0 |
| 1-Stearoyl-2-arachidonoyl-sn-glycerol | 0 |
| Glucocerebrosides | 0 |
| Galactocerebrosides | 0 |
| Phosphatidylserine | 1 |
| Phosphatidylcholine | 0 |
| Phosphatidylethanolamine | 0 |

$^a$Primarily 1-palmitoyl-2-linoleoyl
$^b$Primarily 1-stearoyl-2-arachidonyl.

Various PtdIns-related compounds were tested as possible inhibitors of this purified PtdIns 4-kinase. A concentration of PtdIns of 0.1 mg/ml was used in these tests to accentuate possible competitive inhibition by potential inhibitors (Table IV). Neither PtdIns-4-P or PtdIns-4,5-P$_2$ were effective inhibitors in this assay system. At approximately a 5-fold molar excess of either PtdIns-4-P or PtdIns-4,5-P$_2$, only 42% and 59% inhibition were observed, respectively. At concentrations approximately 10-fold above the PtdIns concentration, inositol, Ins-1P, Ins-1,4-P$_2$, glycerophospho-D-myo-inositol and inositol 2,2'-anhydro-2-C-hydroxymethyl were ineffective as inhibitors.

TABLE IV

Effect of Potential Inhibitors on PtdIns 4-Kinase Activity

| Potential inhibitor | | Relative activity % |
|---|---|---|
| No additions | | 100 |
| PtdIns-4-P | 0.02 mg/ml | 99 |
|  | 0.10 mg/ml | 105 |
|  | 0.50 mg/ml | 58 |
| PtdIns-4,5-P$_2$ | 0.02 mg/ml | 109 |
|  | 0.10 mg/ml | 101 |
|  | 0.50 mg/ml | 41 |
| Inositol | 1.0 mM | 114 |
| Ins-1-P | 1.0 mM | 89 |
| Ins-1,4-P$_2$ | 1.0 mM | 98 |
| Glycerophospho-D-myo-inositol | 1.0 mM | 86 |
| Inositol 2,2'-anhydro-2-C-hydroxymethyl | 1.0 mM | 118 |

Various other examples will be apparent to the person skilled in the art after reading the present disclosure without departing from the spirit and scope of the invention and it is intended that all such other examples be included within the scope of the apended claims.

What is claimed is:

1. A purified bovine uterus derived phosphatidylinositol 4-kinase having the following characteristics:
   (a) molecular weight of about 55 kDa as determined by sodium dodecylsulfate polyacrylamide gel electrophoresis;
   (b) $K_m$ of about 18 µM for ATP;
   (c) $K_m$ of about 22 µg/ml for phosphatidylinositol;
   (d) pH optimum of about 6.0 to 7.0;
   (e) activated by $Mg^{2+}$;
   (f) inhibited by $Ca^{2+}$;
   (g) utilizes ATP and 2'-deoxy-ATP as phosphoryl donors and specifically phosphorylates phosphatidylinositol on the 4-position; and
   (h) essentially free of phosphatidylinositol4-phosphate 5-kinase activity as determined by treatment with phorphoryl donors ADP, GTP, ITP or CTP.

* * * * *

UNITED STATES PATENT AND TRADEMARK OFFICE
CERTIFICATE OF CORRECTION

PATENT NO. : 5,001,064

DATED : March 19, 1991

INVENTOR(S) : Thomas F. Deuel

It is certified that error appears in the above-identified patent and that said Letters Patent is hereby corrected as shown below:

col. 3, lines 5-7, "( , BisTris-HCl ( ), or Tris-HCl ( )" should read --(●), BisTris-HCl (■), or Tris-HCl (▲)--. col. 5, line 34, "Trion" should read --Triton--.

Signed and Sealed this

Third Day of August, 1993

Attest:

MICHAEL K. KIRK

Attesting Officer     Acting Commissioner of Patents and Trademarks